United States Patent
Noda

(10) Patent No.: US 10,416,134 B2
(45) Date of Patent: Sep. 17, 2019

(54) CHROMATOGRAM DATA PROCESSING METHOD AND CHROMATOGRAM DATA PROCESSING APPARATUS

(71) Applicant: SHIMADZU CORPORATION, Kyoto-shi, Kyoto (JP)

(72) Inventor: Akira Noda, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 273 days.

(21) Appl. No.: 15/508,285

(22) PCT Filed: Sep. 3, 2014

(86) PCT No.: PCT/JP2014/073196
§ 371 (c)(1),
(2) Date: Aug. 7, 2017

(87) PCT Pub. No.: WO2016/035167
PCT Pub. Date: Mar. 10, 2016

(65) Prior Publication Data
US 2017/0336370 A1    Nov. 23, 2017

(51) Int. Cl.
*G01N 30/86* (2006.01)
*G01N 30/46* (2006.01)

(52) U.S. Cl.
CPC ......... *G01N 30/8631* (2013.01); *G01N 30/86* (2013.01); *G01N 30/8675* (2013.01); *G01N 30/463* (2013.01)

(58) Field of Classification Search
CPC .............. G01N 30/86; G01N 30/8675; G01N 30/8631; G01N 30/8679; G01N 30/463
See application file for complete search history.

(56) References Cited

U.S. PATENT DOCUMENTS

| 5,644,503 A * | 7/1997 | Ito ........... G01N 30/8624 702/22 |
| 2014/0257712 A1 | 9/2014 | Mito et al. |
| 2016/0224830 A1 * | 8/2016 | Noda ........... G01N 30/8634 |

FOREIGN PATENT DOCUMENTS

| JP | 8-15247 A | 1/1996 |
| WO | 2013/035639 A1 | 3/2013 |

OTHER PUBLICATIONS

Bilmes et al., "A Gentle Tutorial of the EM Algorithm and its Application to Parameter Estimation for Gaussian Mixture and Hidden Markov Models," International Computer Science Institute; TR-97-021, Apr. 1998, 15 pages.
(Continued)

*Primary Examiner* — Bryan Bui
(74) *Attorney, Agent, or Firm* — Sughrue Mion, PLLC

(57) ABSTRACT

The EM algorithm for a Gaussian mixture model is applied to the separation of peaks that overlap one another on a chromatogram. However, the number of overlapping components is unknown. Thus, a suitable number of models is set, and the fitting of model parameters is performed while an actually measured signal is appropriately divided for each model by the EM algorithm. Then, when a solution converges, a determination is made as to whether a peak-like waveform is present in a residue signal that is not divided. When the peak-like waveform is present, a peak model is added. The EM algorithm is executed again. In the M step, optimization is performed using, not only a simple Gaussian function, but also a modified Gaussian function assuming a tailing. In the M step, the estimation of a spectrum assuming a chromatogram and the estimation of a chromatogram assuming a spectrum are repeatedly performed.

9 Claims, 10 Drawing Sheets

(56) References Cited

OTHER PUBLICATIONS

McLachlan et al., "The EM Algorithm and Extensions," Wiley Series in Probability and Statistics, 2008.
Written Opinion for PCT/JP2014/073196 dated Dec. 9, 2014. [PCT/ISA/237].

* cited by examiner

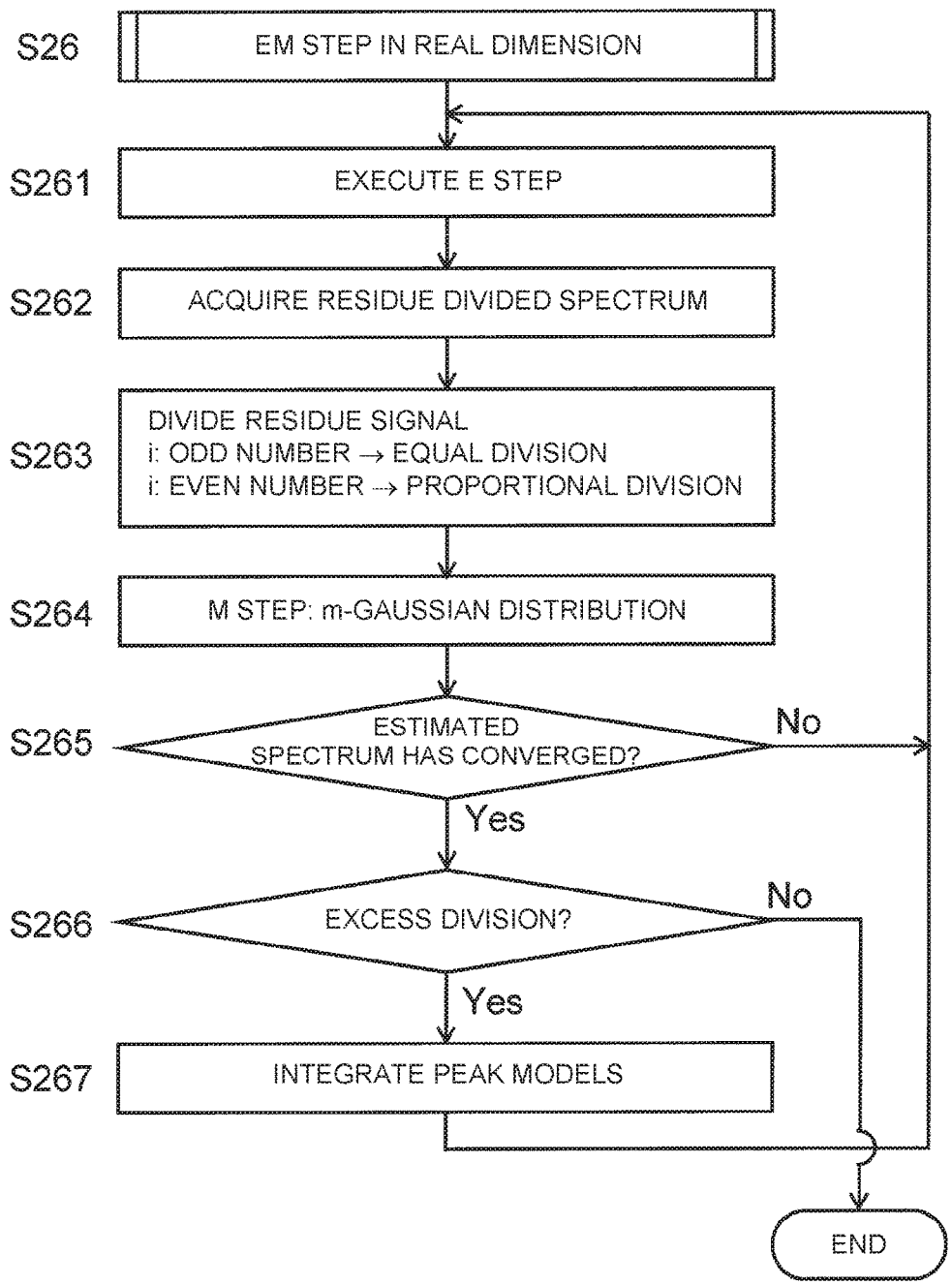

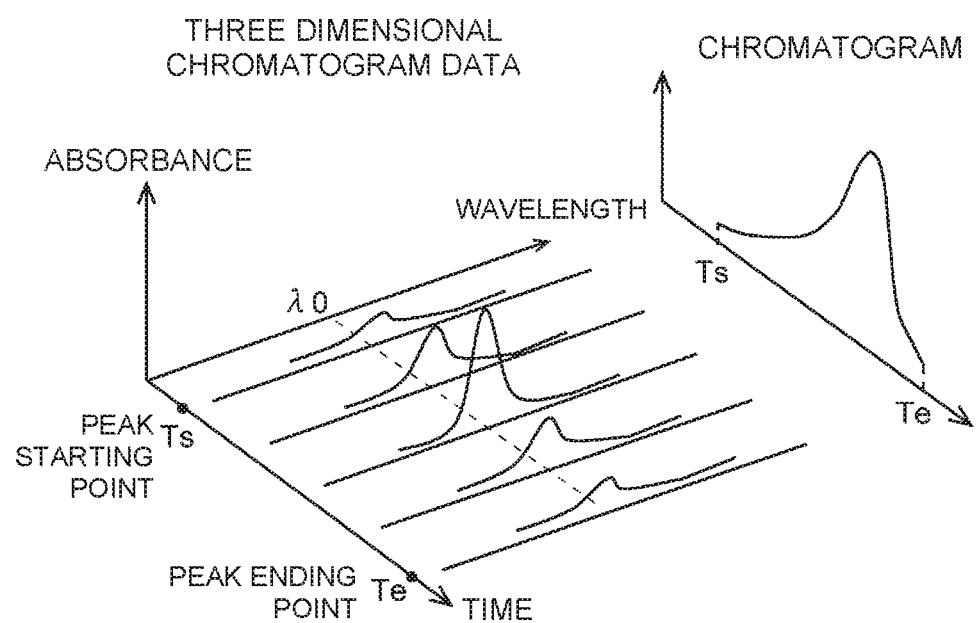

CHROMATOGRAM DATA PROCESSING METHOD AND CHROMATOGRAM DATA PROCESSING APPARATUS

TECHNICAL FIELD

The present invention relates to a chromatogram data processing method and a chromatogram data processing apparatus for processing chromatogram data collected with an analyzer such as a liquid chromatograph (LC) or a gas chromatograph (GC), or a comprehensive two-dimensional gas chromatograph (also called a GC×GC) or a comprehensive two-dimensional liquid chromatograph (also called a LC×LC) including a multichannel detector such as a photodiode array (PDA) detector, or a mass spectrograph, as a detector, more specifically relates to a chromatogram data processing method and chromatogram data processing apparatus for separating peaks originating from different components that overlap one another on a chromatogram or a spectrum.

BACKGROUND ART

In a liquid chromatograph including a multichannel detector such as a PDA detector, an absorption spectrum is repeatedly acquired for sample solution eluted from the outlet of a column, with a time point of injecting a sample into a mobile phase regarded as a starting point, to obtain three dimensional chromatogram data in three dimensions: time, wavelength, and absorb (signal intensity). In a liquid chromatograph or a gas chromatograph including a mass spectrograph as a detector, namely a liquid chromatograph mass spectrograph or a gas chromatograph mass spectrograph, scan measurement is repeated within a predetermined mass-to-charge ratio range using the mass spectrograph to obtain three dimensional chromatogram data in three dimensions: time, mass-to-charge ratio, and signal intensity (ion intensity). In a comprehensive two-dimensional gas chromatograph or a comprehensive two-dimensional liquid chromatograph, further, three dimensional chromatogram data substantially in three dimensions: retention times and signal intensities in a first dimension column and a second-dimension column that have mutually different separate characteristics is obtained.

In the following, description will be made, by way of example, about a liquid chromatograph including a PDA detector (hereinafter, a liquid chromatograph including a PDA detector will be simply referred to as a liquid chromatograph unless particularly specified) as an analyzer with which three dimensional chromatogram data is obtained. It should be noted that the same discussion applies to liquid chromatograph mass spectrographs, gas chromatograph mass spectrographs, comprehensive two-dimensional liquid chromatographs, and comprehensive two-dimensional gas chromatographs as well.

FIG. 13A is a schematic diagram of three dimensional chromatogram data obtained with the liquid chromatograph described above. From the three dimensional chromatogram data, by extracting absorbance data at a specific wavelength (e.g., λ0) in a time direction, it is possible to create a wavelength chromatogram (hereinafter, simply referred to as a chromatogram) showing the relationship between measurement time point (i.e., retention time) and absorbance at the specific wavelength λ0 as illustrated in FIG. 13B. In addition, from the three dimensional chromatogram data, by extracting data representing absorbance at a specific time point (measurement time point) in a wavelength direction, it is possible to create an absorption spectrum (hereinafter, simply referred to as a spectrum) showing the relationship between wavelength and absorbance at the time point. In other words, the three dimensional chromatogram data illustrated in FIG. 13A can be considered to include spectrum information in the wavelength direction and chromatogram information in the time direction.

The quantity determination of a known target component contained in a sample with such a liquid chromatograph normally involves creating a chromatogram at an absorption wavelength at which the largest absorption of light by the target component appears. The quantity determination generally involves finding a starting point Ts and an ending point Te of a peak originating from the target component on the chromatogram, calculating the area value of the peak, and matching the peak area value with a calibration curve determined in advance so as to calculate a quantitative value.

When the quantity of a target component contained in the sample is determined, there is no problem when the peak that appears in the created chromatogram originates from only the target component. However, the peak does not always originate from a single component (target component), and it is often the case that a signal of an impurity out of the analyst's concern (broadly speaking, a component other than the target component) is included. If the analyst performs quantitative calculation without noticing it, the quantitative calculation lacks accuracy. Thus, prior to quantitative calculation, determination is normally made as to whether a peak appearing on a chromatogram originates from only a target component or includes another component, which is called peak purity determination. When a peak in question is overlapped with a peak originating from a component other than the target component, peak separation processing for separating the peak originating from the target component and the peak originating from the other component from each other is performed to obtain a highly pure peak originating from only the target component. Then the quantitative calculation is performed based on the peak.

As the peak purity determination processing and the peak separation processing, various techniques have been known and reduced to practical use.

For example, in the peak separation processing described in Patent Literature 1, when an analyst specifies an absorption wavelength of a target component, a differential value in the wavelength direction in the vicinity of the absorption wavelength is calculated for each of spectra that lines up in a time direction, and a differential chromatogram composed of the differential values arranged in the time direction is generated. If a peak appearing on the spectrum at the position of the absorption wavelength includes that of another component, the differential chromatogram is not flat but shows a peak. Thus, in accordance with whether a peak is present or absent on the differential chromatogram, determination is made as to whether the peak includes one originating from another component, and by making use of the waveform profile or the like of the peak on the differential chromatogram, the peaks of a plurality of components are separated from one another on a spectrum or a chromatogram.

However, such a technique requires an analyst to specify an absorption wavelength specific to a target component by themselves, which requires experience and skill to some extent of the analyst. In other words, manual operation by an analyst who is skilled in analyzing operation to some extent is necessary. In addition, although this method of peak separation processing can separate a peak of two components overlapping with one another, it is difficult to separate a peak of three or more components overlapping with one another.

Another well-known technique for the peak separation processing is a technique using deconvolution. For example, in the technique described in Patent Literature 2, an obtained chromatogram is subjected to deconvolution processing, multivariate analysis processing (factor analysis), or the like using a Gaussian function as a rough chromatogram waveform profile. From the result of the processing, a spectrum waveform with no overlap of components is first determined. Then, based on the obtained spectrum, a chromatogram waveform is estimated, and peaks on the chromatogram are separated from one another.

However, such a technique in which a spectrum is estimated first using the deconvolution processing, and then a chromatogram waveform is estimated using the estimated spectrum waveform involves a problem when a shoulder peak appears in the tailing of a chromatogram peak in that no solution is calculable in principle. This results in a failure to perform an appropriate peak separation. An example will be described with reference to FIG. 14A to FIG. 14D.

FIG. 14A illustrates a function including a shoulder peak expressed by $\exp(-x^2)+0.1*\exp(-(x-3)^2)$, where x denotes a time on the horizontal axis. This waveform is multiplied by an impulse response expressed by $\exp(-x)$ illustrated in FIG. 14B, and a resultant waveform is illustrated in FIG. 14C. This waveform is subjected to ideal deconvolution processing using a Gaussian function, and a waveform illustrated in FIG. 14D is obtained. The waveform illustrated in FIG. 14D is not a simple decay curve. This indicates that even performing the deconvolution processing lets the component of a main peak be mixed in a spectrum at a retention time corresponding to the shoulder peak.

In the technique described in Patent Literature 2, in an estimation of a highly pure spectrum by excluding overlapping component, nonnegative limitation is imposed such that the elements of the spectrum are limited to positive values. However, the spectra obtained with a PDA detector, which can be regarded as multidimensional vectors, normally contain a lot of mutually dependent components. Thus, only by setting up a condition such as a simple nonnegative limitation, spectra originating from different components remain difficult to separate. In other words, without imposing limitation other than the nonnegative limitation that makes a chromatogram waveform profile natural (a waveform expected of a chromatogram), it is difficult to subtract only a spectrum component originating from a main peak from a spectrum observed at a retention time corresponding to the top of a shoulder peak.

For such reasons, the technique described in Patent Literature 2, as well as all techniques that employ procedures in which a pure spectrum is first estimated before the determination of a chromatogram waveform profile cannot handle a shoulder peak occurring in a tailing of a certain peak appropriately and is considered to be unsuitable for the separation of peaks in a chromatogram having such a waveform profile.

CITATION LIST

Patent Literature

[Patent Literature 1] WO 2013/035639 A
[Patent Literature 2] JP 08-015247 A

Non Patent Literature

[Non Patent Literature 1] Geoffrey J. McLachlan et, al, The EM Algorithm and Extensions, Wiley Series in Probability and Statistics, 2008
[Non Patent Literature 2] J. A. Bilmes, A Gentle Tutorial of the EM Algorithm and its Application to Parameter Estimation for Gaussian Mixture and Hidden Markov Models, Technical Report TR-97-021, International Computer Science Institute and Computer Science Division, University of California at Berkeley, 1998

SUMMARY OF INVENTION

Technical Problem

An object of the present invention, which has been made to solve the problems described above, is to provide a chromatogram data processing method and a chromatogram data processing apparatus that provides, based on the three dimensional chromatogram data described above, a chromatogram or a spectrum in which peaks originating from sample components are appropriately separated, in an automatic manner, that is, dispensing with inputting entries and the like that involve cumbersome determination by an analyst, even for a peak consisting of a plurality of (three or more) peaks overlapping one another or a peak in the tailing of which a shoulder peak is present.

Solution to Problem

In general, in a chromatogram or a spectrum, the shape of a pure peak originating from a component (i.e., without an overlap of another component be approximately expressed by a Gaussian function. Therefore normally, in both of a chromatogram and a spectrum, the shape of a peak consisting of overlapped peaks originating from a plurality of components can be regarded as a Gaussian mixture model (GMM) obtained by linearly combining a plurality of Gaussian functions.

As a technique to derive a likely Gaussian mixture model for a certain signal waveform given, an expectation maximization (EM) algorithm for a Gaussian mixture model is well known.

The EM algorithm is one of iterations, which is a technique to determine a maximum likelihood estimate solution by repeating two steps: an expectation value (E) step of calculating an expectation value of a likelihood function in terms of conditional probability; and a maximization (M) step of determining a solution that maximizing the expectation value, and which is described in detail in various literature such as Non-Patent Literature 1 and Non-Patent Literature 2. In the EM algorithm for a Gaussian mixture model, an optimal number of models is normally given in advance as one of calculation conditions. Meanwhile, the peak separation processing of interest here has characteristics on data structure in that one of two-dimensional directions in three dimensional chromatogram data is chromatogram information, another two-dimensional direction is spectrum information, and they are information of totally different kinds, as well as characteristics in that the number of models of the Gaussian mixture model, namely the number of overlapped peaks itself is unknown. Thus, an EM algorithm for a normal Gaussian mixture model cannot be applied as it is.

Thus, the present inventor improved and modified the EM algorithm for a Gaussian mixture model so that it supports the characteristics of the data to deal with and the objective of the data processing and made it possible to estimate, with high accuracy, pure chromatograms respectively originating from a plurality of components that overlap one another timewise on chromatograms, and to separate the peaks favorably.

That is, the present invention made to solve the problems described above is a chromatogram data processing method for processing three dimensional chromatogram data that is collected for a sample to be measured and has dimensions of time, signal intensity, and a third dimension, the chromatogram data processing method performing, for example, as with an expectation maximization (EM) algorithm for a Gaussian mixture model, peak model function fitting in two steps so as to separate peaks originating from a plurality of components contained in the sample, the peaks overlapping one another on a chromatogram having axes representing time and signal intensity, respectively, the chromatogram data processing method including:

a) a data dividing step of dividing given three dimensional chromatogram data for one or more components and determining three dimensional chromatogram data for each component, based on a waveform profile model that is one of an estimation result given in advance and an estimation result by a fitting step to be described later, the waveform profile model being for a waveform profile of a chromatogram having axes representing time and signal intensity, respectively, and a waveform profile of a spectrum having axes representing third dimension and signal intensity, respectively;

b) a fitting step of, on a chromatogram and a spectrum determined from the three dimensional chromatogram data for each component obtained by the data dividing step, performing fitting of chromatogram waveform profile and spectrum waveform profile so as to correct parameters of a waveform profile model corresponding to each component, the fitting step repeating a first step and a second step, the first step being a step of determining a spectrum waveform by a least squares method on assumption that the chromatogram waveform profile is correct, the second step being a step of determining a chromatogram waveform by least squares method on assumption that the spectrum waveform profile is correct, so as to increase a likelihood of the fitting; and c) a contained component determining step of repeatedly performing the data dividing step and the fitting step a specified number of times or until a solution supposedly converges, then filtering the given three dimensional chromatogram data so as to extract or enhance a spectrum component orthogonal to a spectrum corresponding to each component obtained at a time point, and determining whether still another component is contained in the sample based on a height of a peak-like waveform appearing in data after the filtering.

Specifically, in the chromatogram data processing method according to the present invention, the data dividing step corresponds to the E (expectation value) step in the EM algorithm, and the fitting step corresponds to the M (maximization) step in the EM algorithm.

In the case of collecting the three dimensional chromatogram data by repeatedly acquiring an absorption spectrum or a fluorescence spectrum with a detector such as a PDA detector for a sample containing different components separated in a time direction in a column of a chromatograph, the third dimension described above means wavelength.

In the case of collecting the three dimensional chromatogram data by repeatedly acquiring a mass spectrum with a mass spectrograph for a sample containing different components separated in a time direction in a column of a chromatograph, the third dimension described above means mass-to-charge ratio m/z.

Furthermore, in the case of collecting the three dimensional chromatogram data with a comprehensive two-dimensional chromatograph, the third dimension described above means time (retention time). In this case, two of the three dimensions mean time, one of which means a first retention time of a long time interval, and the other of which means a second retention time that represents a short time interval in one time interval of the first retention time.

The three dimensional chromatogram data mentioned here may be data obtained with a multichannel detector such as a PDA detector, or a mass spectrograph for a sample introduced by the flow injection analysis (FIA) method and not subjected to component separation, instead of a sample subjected to component separation through a column of a chromatograph. In other words, in the case where only a single component is included, as long as the data is data that varies in component concentration with time in the form of a mountain shape, which can be approximated as a Gaussian function, the data can be processed in the chromatogram data processing method and the chromatogram data processing apparatus according to the present invention.

In the chromatogram data processing method according to the present invention, by repeating the estimation of a peak model in the fitting step and the estimation of the mixing ratio of the peak model in the data dividing step, a chromatogram peak shape and a spectrum shape are both estimated based on the input three dimensional chromatogram data, and based on the result of the estimation, the peak separation is performed. At this point, by alternately repeating the estimation of a chromatogram waveform and the estimation of the spectrum waveform in the fitting step, the accuracy for the respective waveform profiles can be improved. By the repetition, even a tailing including a shoulder peak can be subjected to peak separation appropriately.

When the mixing ratio of the peak model on the assumption about the peak model at that point is determined by repeating the fitting step and the data dividing step as appropriate, a residue of given three dimensional chromatogram data is obtained in the contained component determining step. If the assumption about a peak model waveform is appropriate, and the division of input data is also appropriate, the residue should be substantially constant. Meanwhile, if a peak-like waveform is observed in the residue, the assumption about the peak model waveform is estimated to be inappropriate, and the inclusion of still another component is inferred because the assumption for the number of models at that point is considered to be highly likely to be inappropriate. Then, under the condition having an increased number of peak models, the repetition of the estimation of a peak model in the fitting step and the estimation of the mixing ratio of the peak model in the data dividing step is performed again.

Executing the EM algorithm while increasing the number of peak models in accordance with the determination based on the residue in such a manner makes it possible to bring the solution for the peak separation close to an optimum solution. As a result, an appropriate peak separation can be performed even when the number of overlapped components is unknown, or even when a lot of (three or more) components overlap one another.

In addition, in the chromatogram data processing method according to the present invention, when it is determined that another component is contained in the sample, the contained component determining step may preferably provide the peak-like waveform appearing in the data after the filtering for processing by the data dividing step, as an initial value of a chromatogram waveform profile of the relevant another component to be added.

This allows the algorithm to be started with a more appropriate initial state at the time when the EM algorithm again is executed again with an increased number of peak models. As a result, the convergence of the solution is improved, and an appropriate peak separation can be performed by a less number of repetitions.

In the chromatogram data processing method according to the present invention, the data dividing step may switch between proportional division and equal division in accordance with a number of repetitions of a step for peak separation processing or how a solution converges, the proportional division dividing a residue signal in accordance with an intensity ratio of a theoretical value at each measurement point, the residue signal being determined by subtracting from the given three dimensional chromatogram data a theoretical value of a signal intensity calculated based on each chromatogram waveform and each spectrum waveform which are the estimation result, the equal division dividing the residue signal equally for each component.

Specifically, when the number of repetitions in the EM algorithm is small, the equal division may be used, and when the number of repetitions becomes large to some extent, the proportional division may be used.

In the chromatogram data processing method according to the present invention, the data dividing step may divide a residue signal in accordance with a least squares approximation using a linear sum of spectra for components, the residue signal being determined by subtracting from the given three dimensional chromatogram data a theoretical value of a signal intensity calculated based on each chromatogram waveform and each spectrum waveform which are the estimation result.

In executing the least squares approximation, a weight given to the spectrum of each component may be limited using one or both of the size of the residue signal and the size of the above-described theoretical value of the signal intensity of each component.

While this dividing method has a high possibility of performing the division with high accuracy in comparison with the equal division or the proportional division described above, all of the residue signals are not necessarily divided. Thus, even in the case of using such a dividing method, it is desirable to combine the equal division or the proportional division described above.

In the chromatogram data processing method according to the present invention, a chromatogram waveform may be determined by adding a chromatogram waveform of each component at an arbitrary ratio, and a stability of a solution by an EM algorithm may be estimated based on a difference between an intensity on the chromatogram waveform and the theoretical value of the signal intensity.

In the chromatogram data processing method according to the present invention, the fitting step may use a model function such as a normal exponential modified Gaussian (EMG) as a chromatogram model waveform, and more preferably, the fitting step may use a database in which chromatogram waveforms each having a peak width, a peak height, and the like that are normalized are stored, and select and use an optimal chromatogram waveform from the database.

This allows utilization of a more practical chromatogram waveform as a peak model and thus improves the accuracy of the fitting furthermore.

With a PDA detector in particular, the linearity drops at a high component concentration, and under the influence of the drop in linearity, a spectrum shape may slightly change. Due to this change, the number of peak models is falsely determined in some cases in the contained component determining step even when the number of peak models is actually correct.

Thus, in the chromatogram data processing method according to the present invention, when a peak-like waveform is present in the residue signal, determination may be made as to whether the peak-like waveform is attributable to linearity degradation of a detector based on a ratio of a size of each element in an eigenvalue obtained by performing principal component analysis on the residue signal in a form of a matrix, and it may be concluded that there is no component to be added when the peak-like waveform is estimated to be attributable to the linearity degradation. An excess peak separation can be thereby avoided.

A chromatogram data processing apparatus according to the present invention is an apparatus for performing the above-descried chromatogram data processing methods according to the present invention, the chromatogram data processing apparatus processing three dimensional chromatogram data that is collected for a sample to be measured and has dimensions of time, signal intensity, and a third dimension, the chromatogram data processing apparatus performing, for example, as with the EM algorithm for a Gaussian mixture model, peak model function fitting in two steps so as to separate peaks originating from a plurality of components contained in the sample, the peaks overlapping one another on a chromatogram having axes representing time and signal intensity, respectively, the chromatogram data processing apparatus including:

a) a data dividing unit for dividing given three dimensional chromatogram data for one or more components and determining three dimensional chromatogram data for each component, based on a waveform profile model that is one of an estimation result given in advance and an estimation result by a fitting unit to be described later, the waveform profile model being for a waveform profile of a chromatogram having axes representing time and signal intensity, respectively, and a waveform profile of a spectrum having axes representing third dimension and signal intensity, respectively;

b) a fitting unit for, on a chromatogram and a spectrum determined from the three dimensional chromatogram data for each component obtained by the data dividing step, performing fitting of chromatogram waveform profile and spectrum waveform profile so as to correct parameters of a waveform profile model corresponding to each component, the fitting unit repeating a first step and a second step, the first step being a step of determining a spectrum waveform by a least squares method on assumption that the chromatogram waveform profile is correct, the second step being a step of determining a chromatogram waveform by least squares method on assumption that the spectrum waveform profile is correct, so as to increase a likelihood of the filling; and c) a contained component determining unit for repeatedly performing processing by the data dividing unit and processing by the fitting unit a specified number of times or until a solution supposedly converges, then filtering the given three dimensional chromatogram data so as to extract or enhance a spectrum component orthogonal to a spectrum corresponding to each component obtained at a time point, and determining whether still another component is contained in the sample based on a height of a peak-like waveform appearing in data after the filtering.

Advantageous Effects of Invention

By the chromatogram data processing method and with the chromatogram data processing apparatus according to the present invention, for example, even when a peak that appears on a chromatogram or a spectrum created based on three dimensional chromatogram data collected with a chromatograph using a multichannel detector such as a PDA detector, or a mass spectrograph as a detector consists of overlapped peaks originating from a plurality of (three or more) components or is a peak including a shoulder peak in its tailing, it is possible to separate the overlapped peaks accurately. This allows the quantity determination of a plurality of components contained in a sample to be performed with high accuracy even with, for example, a chromatograph with a poor separating performance.

BRIEF DESCRIPTION OF DRAWINGS

FIG. 12 is a flowchart illustrating the procedure of a process in an EM step in a real dimension in FIG. 9.

FIG. 13A is a schematic diagram illustrating three dimensional chromatogram data obtained by a liquid chromatograph, and FIG. 13B is a diagram illustrating an example of a wavelength chromatogram.

FIG. 14A illustrates an original peak waveform. FIG. 14B illustrates an impulse response waveform, FIG. 14C illustrates a waveform obtained by multiplying the peak waveform in FIG. 14A by the impulse response waveform in FIG. 14B, and FIG. 14D illustrates a waveform of the result obtained by subjecting the peak waveform in FIG. 14C to ideal deconvolution processing using a Gaussian function.

DESCRIPTION OF EMBODIMENTS

Description will be made first about one embodiment of a chromatogram data processing method according to the present invention, with reference to the accompanying drawings.

Figure 2:
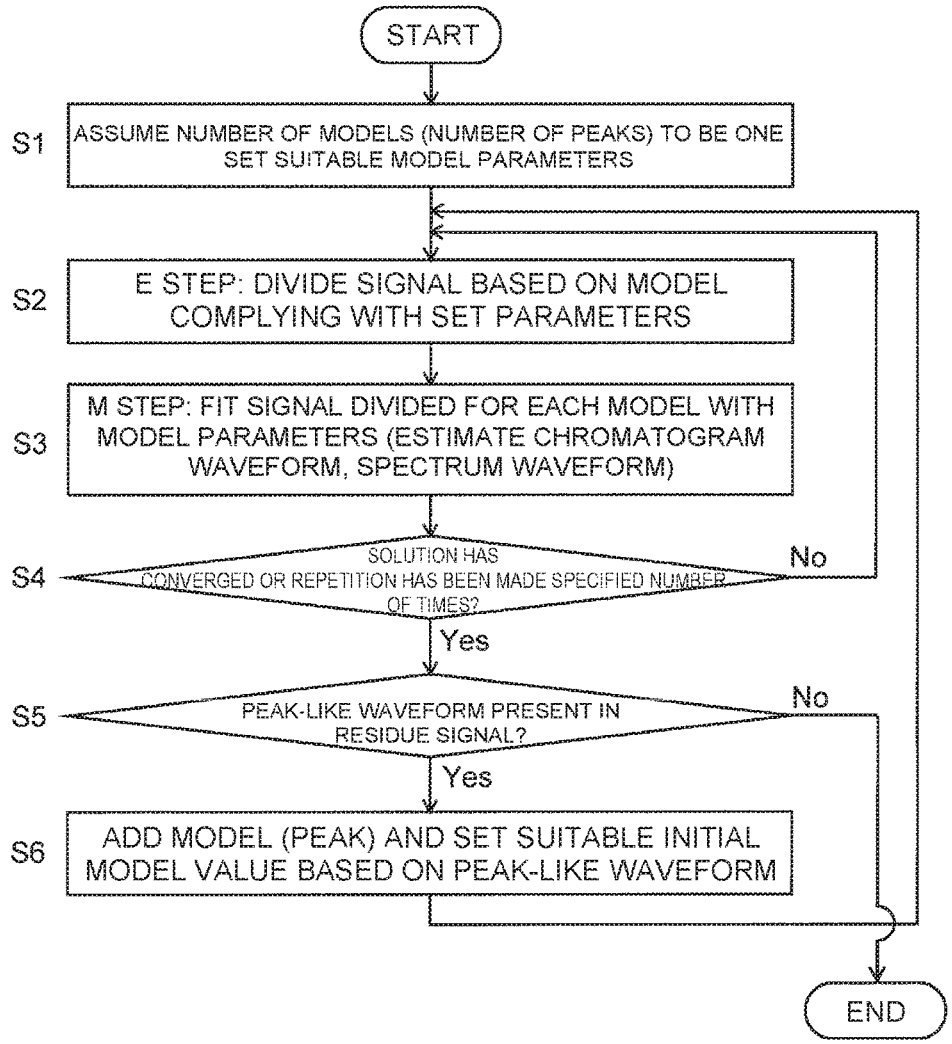
FIG. 2 is a flowchart illustrating a basic procedure of peak separation processing that is an embodiment of the present invention.

This chromatogram data processing method is to perform peak separation processing on the three dimensional chromatogram data illustrated in FIG. 13A, which has been already described, so as to estimate a chromatogram waveform and a spectrum waveform for each component contained in a sample. FIG. 2 is a basic flowchart of this peak separation processing.

Figure 3:
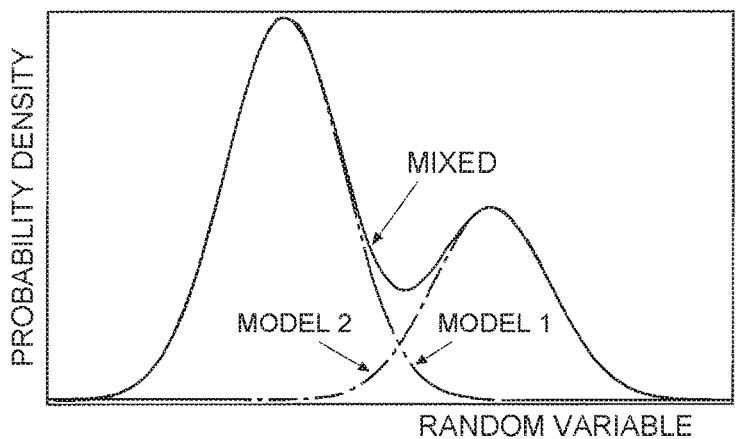
FIG. 3 is a diagram illustrating an example of a chromatogram waveform according to a Gaussian mixture model (in the case of two peaks).

As generally known, the shape of a pure peak appearing on a chromatogram or a spectrum is approximately expressed as a Gaussian function. For this reason, in both of a chromatogram and a spectrum, the overlap of peaks originating from a plurality of components is normally regarded as a Gaussian mixture model obtained by linearly combining a plurality of Gaussian functions. Thus, the EM algorithm for a Gaussian mixture model (GMM) is used here for peak separation on a chromatogram or a spectrum. The EM algorithm is normally an algorithm that repeatedly performs the step of optimizing the parameters of a probability model representing a probability density function of a random variable (i.e., the M step), and the step of optimizing signal separation based on the probability model (i.e., the E step). Here, each probability model represents one peak that is made up of three dimensional chromatogram data corresponding to one component, and the data includes chromatogram waveform information and spectrum waveform information. Modeling is then performed on the assumption that an observation signal is the mixture of a plurality of probability models at their respective concentrations. FIG. 3 illustrates an example of two probability models (models 1 and 2) and a waveform obtained by mixing them.

The EM algorithm for a GMM itself has been used in various fields. In general, the EM algorithm for a GMM is known for needing to be processed with an appropriate number of probability models and their rough initial values given, otherwise the algorithm falls into a local solution. However, the peak separation processing has characteristics in that a data structure includes chromatogram information as well as spectrum information, and in addition, characteristics in that the number of probability models, namely the number of overlapped chromatogram peaks is unknown to begin with. Thus, to solve the problem of unknown number of optimal probability models, various characteristics and modifications as will be described below are added to the underlying EM algorithm for a GMM, so that a favorable peak separation processing is performed.

As described above, the EM algorithm for a GMM and the calculating method therefor are described in detail in various literature including Non-Patent Literature 1 and Non-Patent Literature 2, and thus the detailed description thereof is omitted.

Here, as described above, the number of components that overlap in the same retention time range and the same wavelength range, namely the number of peak models after the peak separation processing is unknown before the processing. Thus, assuming that the number of peaks is one, the processing is started with the number of peak models=1. In addition, suitable model parameters of one of the peaks are set (step S1).

Rather than setting the initial value of the number of peaks at one, the initial value of the number of peaks may be set at a result obtained through peak separation by an existing technique, or peak splitting using straight lines, which is generally performed in signal processing of a chromatogram. In other words, in the case where it is known that the number of peaks is not below a certain value with a high probability, setting the initial value at the certain value can lead to a final result more efficiently (i.e., in a short processing time).

Next, as the E step of the EM algorithm, an input chromatogram signal is divided based on a peak model complying with the set model parameter (step S2). When step S2 is executed with the number of peaks being one, the division of the signal is not needed, and thus step S2 is substantially skipped.

In this E step, ideally, the input chromatogram signal multiplied by a spectrum represented by peak model parameters is a divided signal. Here, furthermore, the height of a spectrum from each peak model is optimized with error least square criterion. For a general GMM, a residue signal that is not divided and but remains after the optimization of the GMM is divided in proportion to a weight given to each peak model. Although such division may be used here, it is more preferable to subject a residue signal after subjected to an ideal signal division to signal division by three kinds of methods described below: proportional division, equal division, and spectrum division, as appropriate.

(1) Proportional Division

The proportional division is to perform processing the same as that for a general GMM for each wavelength. In other words, a residue signal obtained based on peak models and a input signal is divided in proportion to the intensities on peak model waveforms.

(2) Equal Division

The equal division is to divide a residue signal of an input signal equally for all peak models. This is effective in particular in the case where the discrepancy between an estimated peak model and an actual value is large, for example, in an initial stage of the EM step.

(3) Spectrum Division

In the spectrum division, at each retention time, a residue signal is regarded as a composite value of the spectra of the peak models, and the magnitudes of the respective spectra are determined by the least squares method. In order to avoid overadaptation, use is made of a restricted least squares method that adds a restriction requiring a weight for each spectrum component to be equal to or less than the scalar product of the residue spectrum and the spectrum of each peak model, or a predetermined value close to the scalar product. Although being a significantly effective signal dividing method, the spectrum division cannot divide the residue signal totally. Thus, a residue signal that remains after the spectrum division needs to be further divided by the proportional division or the equal division.

After the signal is divided to each peak model, as the M step of the EM algorithm, a signal divided to each peak model is subjected to the fitting of a peak model, and model parameters are corrected to increase a likelihood (step S3).

In general, chromatogram data obtained with an ideal liquid chromatograph shows a spectrum specific to each peak model regardless of component concentration and the like. Thus, improved processing is performed here assuming the constraint on spectrum information that each peak model has its specific spectrum without exception.

That is, in step S3, combined use is made of a Gaussian distribution M step in which a peak shape is assumed to be a simple Gaussian function and an m-Gaussian distribution (modified Gaussian distribution) M step in which a peak shape is assumed in advance to have a tailing.

Since a normal Gaussian function cannot express a tailing, the optimization of parameters by the Gaussian distribution M step is inferior in terms of accuracy. Meanwhile, since the Gaussian distribution M step requires only a small number of parameters, the Gaussian distribution M step has an advantage of a low risk of falling into a local solution due to overadaptation. In contrast, the m-Gaussian distribution M step performs the fitting using waveforms that are created based on, rather than ideal Gaussian functions, tailing model functions such as exponential modified Gaussian (EMG) functions, or peak waveforms or the like obtained through actual measurement so as to determine a peak model waveform. For this reason, the m-Gaussian distribution M step can perform the approximation of a peak model waveform with high accuracy in comparison with the Gaussian distribution M step. On the other hand, because of a high degree-of-freedom, the m-Gaussian distribution M step has the drawback of being prone to fall into a local solution due to overadaptation. Thus, here, in the early stage of the EM algorithm where steps S2 and S3 are repeated, use is made of the normal Gaussian distribution M step that emphasizes the stability of the processing more than accuracy, and in the later stage of the EM algorithm, use is made of the m-Gaussian distribution M step that emphasizes accuracy. This enables both of the stability of the processing and the accuracy of the estimation of a peak waveform.

Each M step will be described in detail as follows.

(1) Gaussian Distribution M Step

Normally, for a GMM, fitting of a Gaussian distribution is performed on a probability density function, but here, use is made of, rather than the probability density function, a spectrum at each retention time (i.e., a waveform representing the relationship between wavelength and signal intensity).

Figure 4:
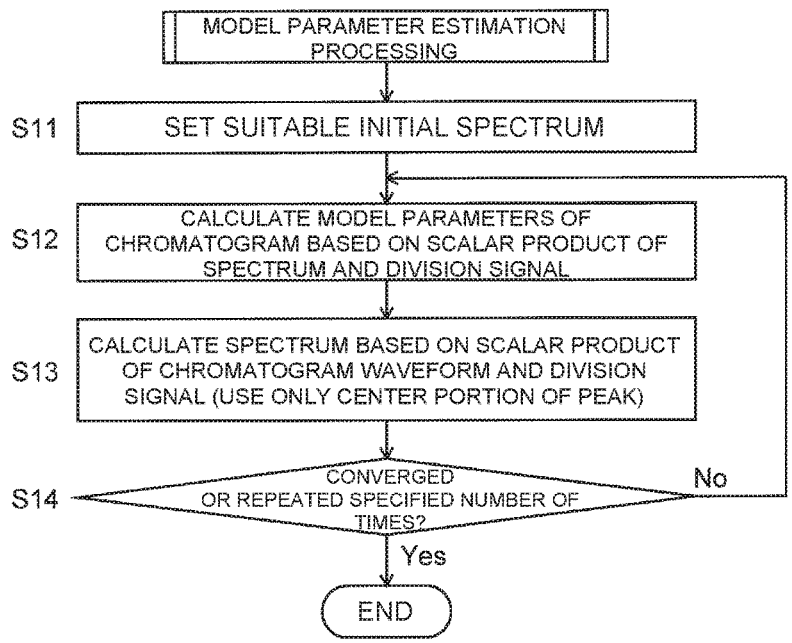
FIG. 4 is a flowchart illustrating parameter estimation processing of a peak model.

FIG. 4 is a flowchart of parameter estimation processing for a peak model at this point.

That is, first, a suitable initial spectrum is set (step S11), and thereafter, on the assumption that a spectrum is known, the scalar product of the spectrum and a division signal is input, the model parameters of an optimal chromatogram peak common to each wavelength are calculated (step S12). This determines a chromatogram waveform temporarily, and subsequently, on the assumption that the model parameters of the chromatogram waveform are known, the scalar product of the chromatogram waveform and the division signal is calculated, which is determined to be an optimal spectrum (step S13). In such a manner, the width and the position of a peak on a chromatogram are estimated as the parameters of a peak model, and at the same time, a spectrum is also estimated. Here, the chromatogram and the spectrum include baseline noise, and thus, use cannot be made of the method for determining model parameters from the moment of a distribution, which is used in a GMM targeting a typical probability distribution. Thus, the position and the width of the peak are estimated using the least squares method.

(2) m-Gaussian Distribution M Step

Except that use is made of a modified Gaussian distribution into which modification factors including a tailing are incorporated as a model function, the objective of this M step is the same as that of above-described Gaussian distribution M step.

In determining the width and the position, and the tailing shape of a peak on a chromatogram, the position and the width of the peak are determined, and thereafter they are checked against a database in which various modified Gaussian distribution model waveforms are stored.

Figure 5:
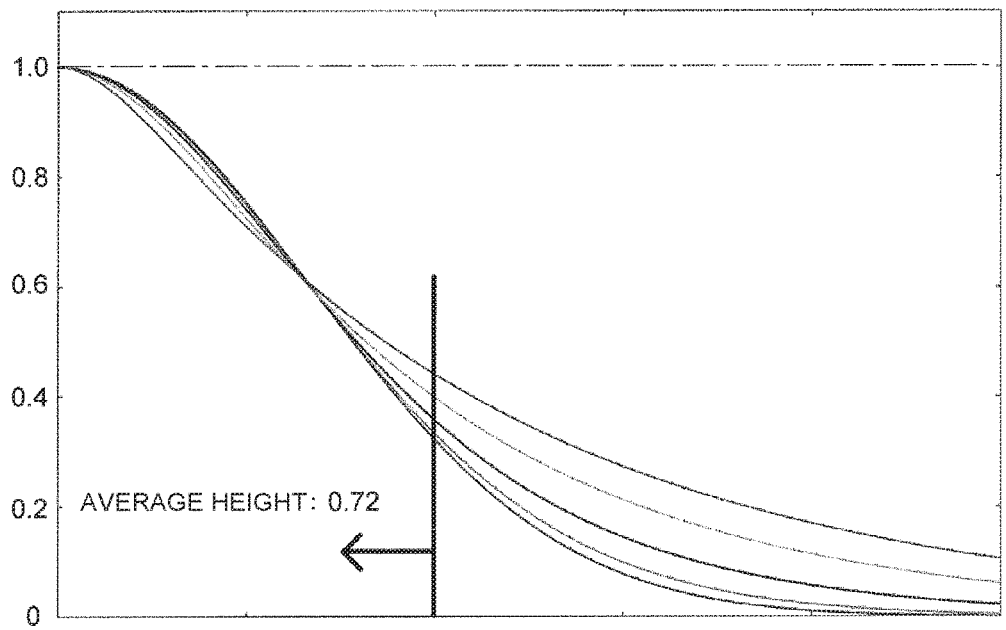
FIG. 5 is an illustrative diagram of estimation processing of a peak width.

The estimation of the position of the peak is made by performing mean shift in a time direction in subsampling units so as to estimate a peak top. Meanwhile, the estimation of the width of the peak is made by determining a width so that, as illustrated in FIG. 5, an average signal height within the width becomes 0.72, assuming that the maximum value of a peak height is 1. This allows a peak width to be determined with high accuracy and more robustly than determining a half width. Of course, values other than 0.72 may be used for the average height.

As for the tailing shape, it may suffice to extract of a waveform having the highest resemblance in shape (the highest in degree of correlation) by checking against the above-described database. This database may be created from a model function with parameters adjusted within a proper range, or may be determined by clustering waveforms that are actually measured. The processing described above may be executed in such a manner as to divide a peak into a former (leading) portion and a latter (tailing) portion and perform the processing on the respective positions, or may be executed in such a manner that does not make such a division but perform the processing on data including the former portion and the latter portion as a set.

After the processes of steps S2 and S3 described above is finished, a determined is made as to whether a solution has converged. Otherwise, if the solution has not converged, a determination is made as to whether the processes of steps S2 and S3 has been repeated a specified number of times (step S4). Then, if the solution has not converged, and the repetition of the processing has not reached the specified number of times, either, the processing returns to step S2. Therefore, when the processing returns from step S4 to S2, step S2 (the E step) is to be executed using the model parameters corrected in step S3 (the) M step).

When the determination in step S4 results in Yes, a residue signal that is left by executing the EM algorithm is obtained, and the presence/absence of a peak-like waveform in the residue signal is determined to judge whether to add a peak model (step S5).

Figure 6:
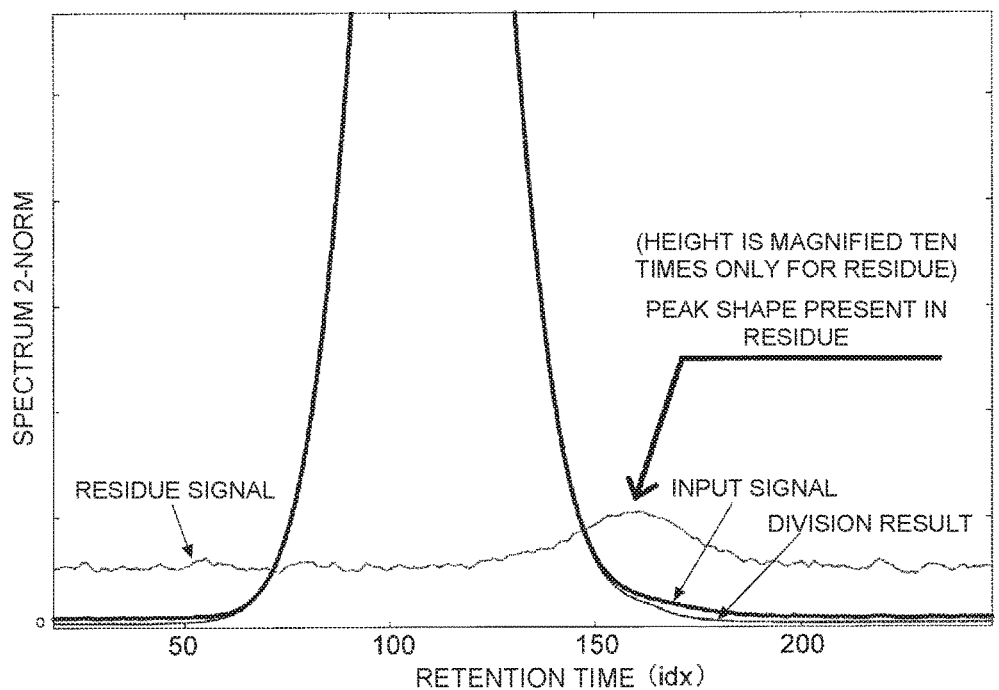
FIG. 6 is a diagram illustrating an example of a spectrum residue chromatogram where a peak-like waveform is present.

Specifically, a spectrum orthogonal to the spectrum of each peak model is extracted from the input chromatogram signal as a residue signal, and the 2-norm of the residue signal is calculated at each retention time. Then, a spectrum residue chromatogram in which the 2-norms of the residue signals are arranged in chronological order is created. In the case where peak models are determined for a plurality of respective components overlapping one another at least on a chromatogram in question, the residue signal becomes substantially zero, or while the residue signal does not become zero due to the influences of background noise and the like, the residue signal has no large fluctuation temporally. Therefore, when a peak-like waveform is observed in the spectrum residue chromatogram, the residue signal can be considered to still include another component remaining. In this case, a new peak model needs to be added. FIG. 6 illustrates an example of a spectrum residue chromatogram in which a peak-like waveform is present.

To determine the presence/absence of a peak-like waveform in the spectrum residue chromatogram, various known peak detecting methods can be used, and here, the presence/absence of a peak-like waveform is determined as follows.

That is, the spectrum residue chromatogram is subjected to peak detection, and a half width including a maximum value (a width at the ends of which signal intensities are 60% of the maximum value) is determined. Then, the 5th-order differentials of signal intensities within the half width are calculated and treated as a noise level, the difference between the maximum value and a minimum value of signals within the half width is compared with the noise level, and when the difference is sufficiently large in comparison with the noise level (e.g., a predetermined times or more of the noise level), the detected peak is determined to be a peak-like waveform.

As described above, when a peak-like waveform is determined to be present in the residue signal in step S5, another overlap of a component is estimated to exist, a model peak is added, with a suitable initial model value set based on the peak-like waveform (step S6), and the processing returns to step S2. Meanwhile, when no peak-like waveform is determined to be present in the residue signal in step S5, the processing is finished determining that the addition of a model peak is not needed.

However, even when a peak-like waveform is present in the residue signal, if the peak height of the peak-like waveform is not more than the SN ratio level of the entire residue signal, the peak is likely to be actually a noise fluctuation. Thus, the residue signal is normalized for each wavelength, and if the spectrum of the residue signal in a maximum-value portion of the peak-like waveform is not more than h noise level described above for every wavelength, the processing is finished as an exception determining that a model peak is not added.

When the processing returns from step S6 to S2, the EM algorithm by steps S2 to S4 described above is repeated again, with the number of peak models incremented by one. Then, when the peak in question enters the state in which no other component is considered to overlap, the determination in step S5 results in No, the processing is finished, and a chromatogram and a spectrum associated with each component is determined.

In the case of using a PDA detector as a detector, it is desirable to consider not only the noise but also the occurrence of a false peak-like waveform accompanied by the deterioration of the detector in linearity.

That is, in general, PDA detectors tend to deteriorate in linearity of detection for a sample at a high concentration. For this reason, a peak-like waveform of a spectrum changes as the component concentration is increased, and in this data processing method presuming that the shape of a spectrum for the identical sample component is unchanged, the change in the peak-like waveform in some cases appears on a residue signal in the form of an unexpected peak-like waveform.

Figure 7:
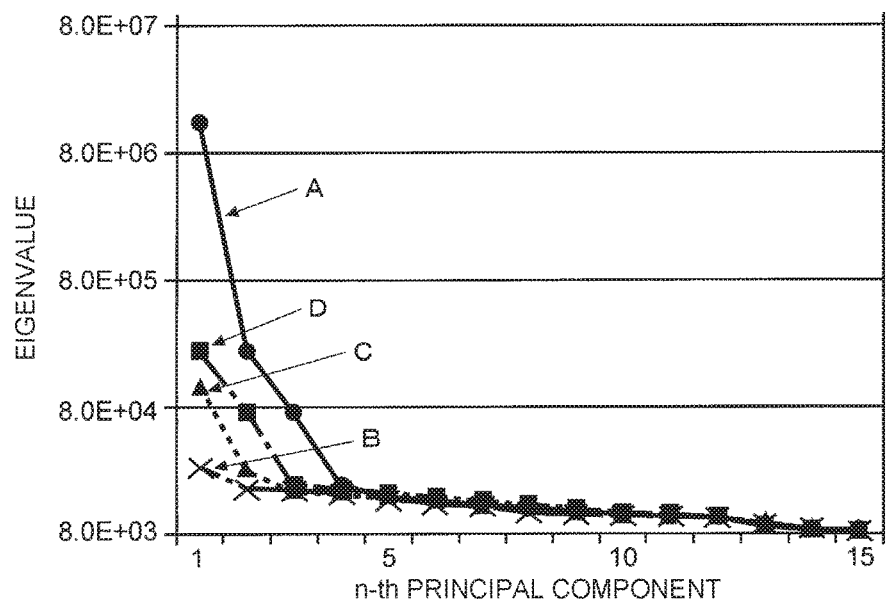
FIG. 7 is a graph illustrating the relationship between principal component and eigenvalue when principal component analysis is performed on a certain input signal.

In the case where the input chromatogram signal is an ideal one, when the signal is subjected to the principal component analysis (PCA), an element appear that has an eigenvalues large by the number of overlapping peaks, and the remaining eigenvalues includes noise. FIG. 7 is a graph illustrating the relationship between principal component and eigenvalue when the principal component analysis is performed on a certain input signal. As illustrated by a line A in FIG. 7, when a detector does not suffer linearity degradation, and the number of overlapping peaks is only one, the eigenvalue of a first principal component is prominently large. In contrast, in the case of a signal in which the number of overlapping peaks is not one, as illustrated by a line B in FIG. 7, the magnitude of the eigenvalue of the first principal component is not necessarily prominently large in comparison with the eigenvalue of a second principal component and the like.

Lines C and D in FIG. 7 show examples of the case where a detector suffers linearity degradation, the line C shows eigenvalues when the linearity degradation is minor, and the line D shows eigenvalues when the linearity degradation is major. From these results, it is understood that, as compared with the eigenvalues in the case of substantially no linearity degradation, the second and third principal components are large, and the larger the degree of the linearity degradation, the larger the second and third principal component becomes. From this fact, it is understood that the determination as to whether elements caused by the linearity degradation of a detector account for a major portion of a residue signal is enabled by determining the eigenvalues of the first to third principal components in the principal component analysis for an input signal.

Thus, in the method of data processing according to the present embodiment, the adoption of the following method suffices from an empirical standpoint. That is, the principal component analysis in 15 dimensions is performed on a input chromatogram signal, and when the eigenvalue of a first principal component in a residue is denoted by $Z_1$, the 2-norm of the eigenvalues of n-th to m-th principal components is denoted by $Z_{n-m}$, and similarly, a variable about an eigenvalue for an input signal is denoted by S, use is made of an index value calculated by the following expressions. Of course, the magnitude of the eigenvalues of the first to third principal components can be calculated using a feature quantity such as moment, which represents a dispersion of distribution.

$$ZR_1 = \text{sqrt}\{(Z_1^2 - Z_{12-15}^2)/(Z_{2-5}^2 - Z_{12-15}^2)\}$$

$$ZR_2 = \text{sqrt}\{(Z_1^2 - Z_{12-15}^2)/(Z_{6-8}^2 - Z_{12-15}^2)\}$$

$$SR_1 = \text{sqrt}\{(S_1^2 - S_{12-15}^2)/(S_{2-5}^2 - S_{12-15}^2)\}$$

$$SR_2 = \text{sqrt}\{(S_1^2 - S_{12-15}^2)/(S_{6-8}^2 - S_{12-15}^2)\}$$

When $ZR_1/SR_1 < 0.5$, and $ZR_2/SR_1 < 0.01$, the deterioration is determined to occur.

If the linearity degradation is concluded to occur in the above-described manner, even when a peak-like waveform is observed in a spectrum residue chromatogram, the cause of peak-like waveform is likely to be attributable to the linearity degradation of a detector. Thus, in such a case, the processing may be finished without executing the addition of a peak model in step S6.

Figure 8:
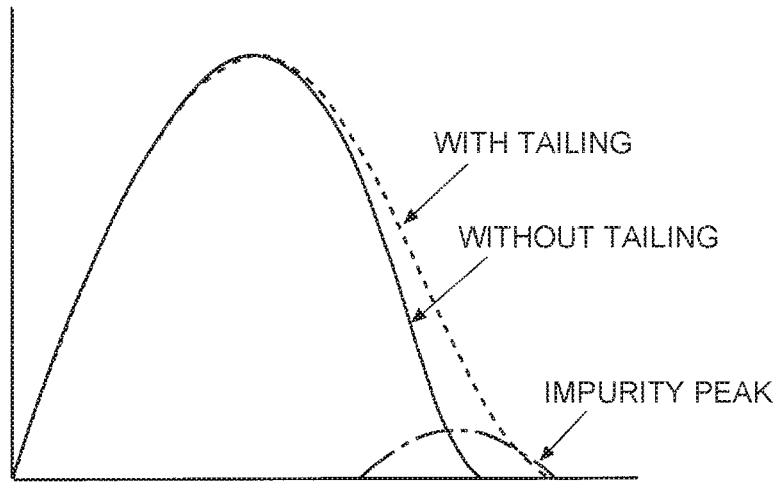
FIG. 8 is a diagram illustrating how an impurity peak on a tailing is.
Figure 9:
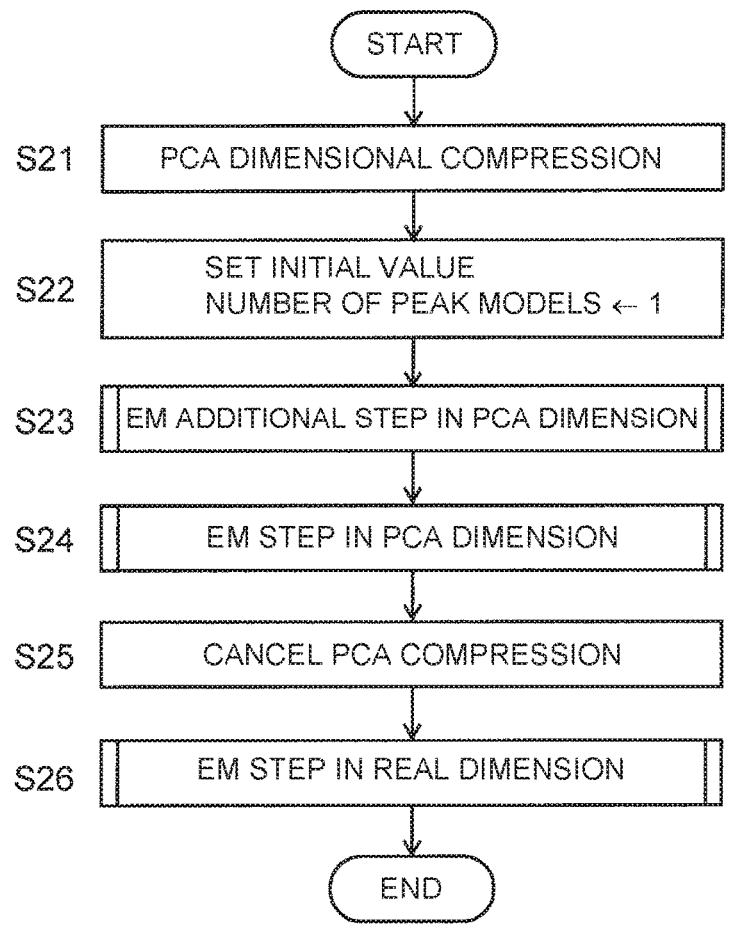
FIG. 9 is a flowchart illustrating peak separation processing in another embodiment.

Since the data processing method according to the present embodiment deals with a tailing of a peak as described above, a solution cannot be determined uniquely but is unstable under a specific condition. For example, a tailing such as an EMG function can be approximated using a plurality of Gaussian functions. For this reason, when one of the plurality of Gaussian functions substantially matches the shape of an impurity peak, adding the spectrum of a principal component peak to the impurity peak brings a nature resultant solution by adjusting the degree of the tailing (see FIG. 8).

This condition that adding the spectrum of the principal component peak to the impurity peak results in a natural waveform profile indicates that, considering the time axis of a chromatogram, adding an impurity peak to some extent does not spoil natural fitting of the chromatogram of a principal component although its tailing changes. Thus, preferably, it suffices to add a step of determining the stability of a solution based on how a square error in the model fitting step increases when the peak model waveform of the chromatogram of an impurity component is added to the peak model waveform of the chromatogram of a principal component.

In the case where a certain peak on a chromatogram is a composite peak of a large peak and a small peak, a problem in the stability of a solution is the fluctuations of the small peak. Thus, the 2-norm of a spectrum is used as the height of each peak model, the amount of fluctuations of a square error in the model fitting step is determined assuming the case where the peak of a smaller chromatogram fluctuates at a constant percentage about ±10%), and the determination of a unstable solution may be made based on the amount of fluctuations.

In the case where the above-described determination of the stability of a solution or the determination of an unstable solution provides the result that a significantly unstable solution is present, and it correlates a spectrum to a certain degree or more, there is the possibility that a peak the number of which should be one by nature is divided into an excessive number of peaks. Thus, it suffices a process for determining such a thing may be added an integrating process for integrating a plurality of peak models may be performed so as to reduce the number of peak models when an excessive division is confirmed.

In an specific application such as a pure product test, when an unstable solution is determined as described above, one needs to know to what degree a solution is unstable within a range, in some cases. This is, for example, the case where such an acceptance determination criterion is set that the unstable solution is accepted if the peak area of an impurity with respect to the peak area of the unstable solution is 1.5 or less, the peak area of an impurity is determined to be 1, and the solution is determined to be an unstable solution. In this case, the determination as to whether the unstable solution can become 1.5 times or more is important.

To support such determination, for example, a range within which a solution is unstable may be investigated using chromatogram waveforms each having a peak height and a peak area that are normalized, and then the range of the solution at each wavelength may be determined in proportion to a signal intensity at each wavelength on a spectrum.

Next, description will be made about a chromatogram data processing method in another embodiment that is built on the chromatogram data processing method in the embodiment described above, and that increases the speed of the processing and includes the additional process described above, with reference to flowcharts illustrated in FIG. 9 to FIG. 12.

In this chromatogram data processing method, for three dimensional chromatogram data, each spectrum is subjected to dimensional compression by principal component analysis (step S21). This is to compress the amount of data to be processed. Then, initial setting in step S22, which is the same as that in step S1 in FIG. 2, is executed, and then EM additional step processing in a PCA dimension is executed (step S23).

Figure 10:
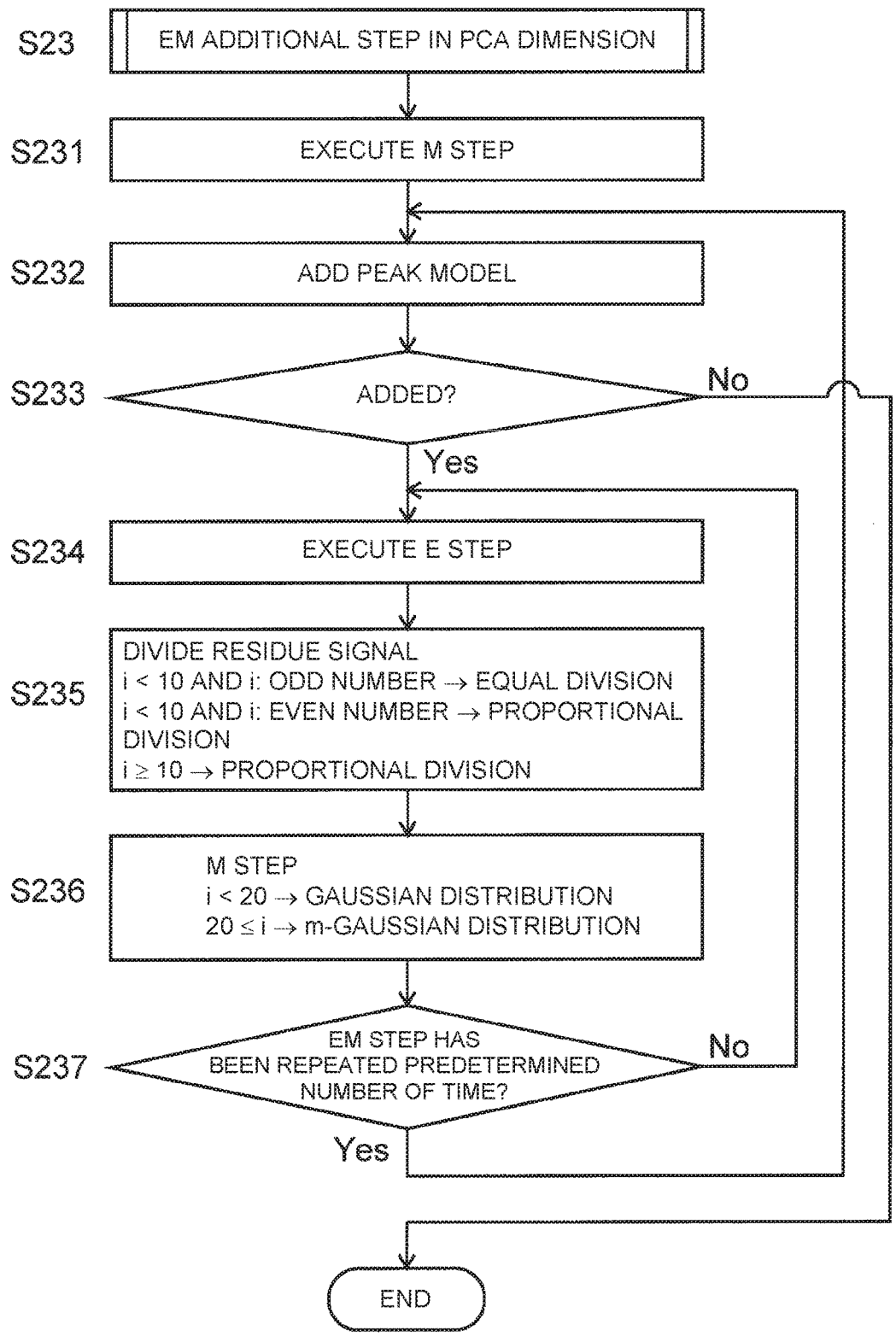
FIG. 10 is a flowchart illustrating the procedure of a process in an EM additional step in a PCA dimension in FIG. 9.

Although this processing starts with the M step as illustrated in FIG. 10, this is because the E step is substantially skipped when the number of peak models is one, which is totally the same as the processing that proceeds as step S1→S2→S3 in FIG. 2. Steps S232 and S233 in FIG. 10 are substantially the same as steps S5 and S6 in FIG. 2, and the process in FIG. 10 in which the processing proceeds to step S234 when the determination in step S233 results in Yes is the same as the process in FIG. 2 in which the processing returns to S2 via step S6 when the determination in step S5 results in Yes.

Here, in the E step in step S234, as the signal division of a residue signal after performing ideal signal division, the equal division and the proportional division are used out of three methods described above. That is, assume that the number of repetitions of steps S234 to S237 is denoted by i, when i is an odd number less than ten, the signal division is performed by the equal division, and when i is an even number less than ten or i is equal to or greater than ten, the signal division is performed by the proportional division (step S235). Then, in the M step in subsequent step S236, when the number of repetitions i is less than 20, the process of the Gaussian distribution M step is executed, and when i is equal to or greater than 20, the process of the m-Gaussian distribution M step is executed (step S236). After the execution of the M step, a determination is made as to whether the number of repetitions i of the EM step has reached a predetermined number (step S237), and when i has not reached the predetermined number, the processing returns to step S234. Here, the predetermined number may be set at, for example, 50. Then, when the determination of step S237 results in Yes, the processing returns from S237 to S232 as the processing proceeds from step S4 to S5 in FIG. 2. Then, when no new peak model needs to be added, the determination in step S233 results in No, the process of the EM additional step in this PCA dimension is finished.

Figure 11:
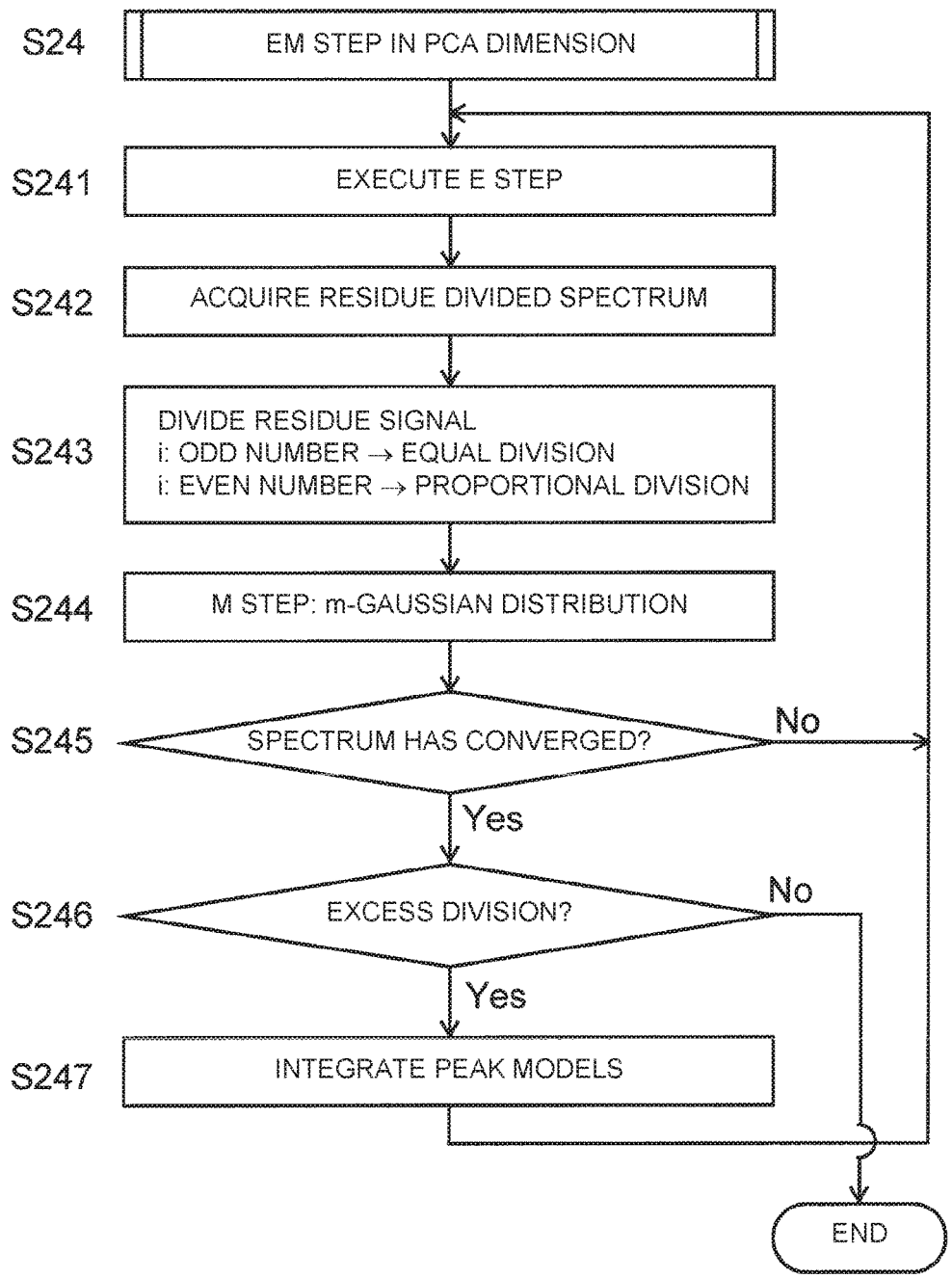
FIG. 11 is a flowchart illustrating the procedure of a process in an EM step in a PCA dimension in FIG. 9.
Figure 14A:
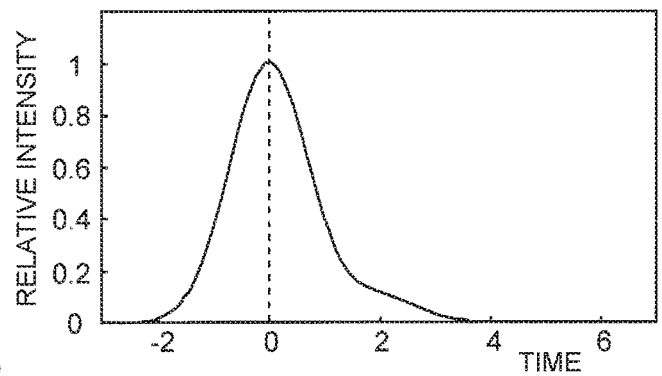
FIG. 14A to FIG. 14D are diagrams illustrating an example of deconvolution processing in the case where a shoulder peak is present on a tailing, where
Figure 14B:
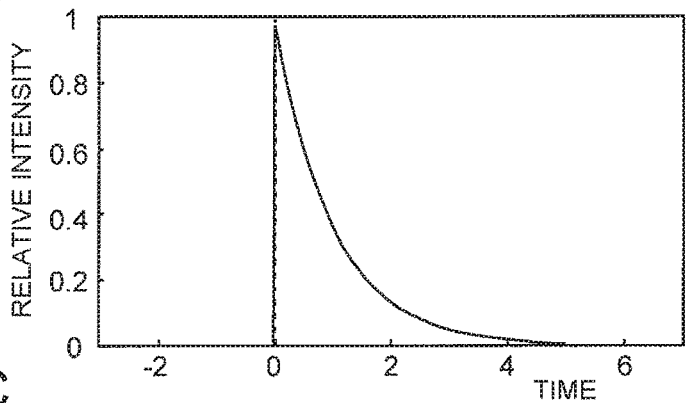
Figure 14C:
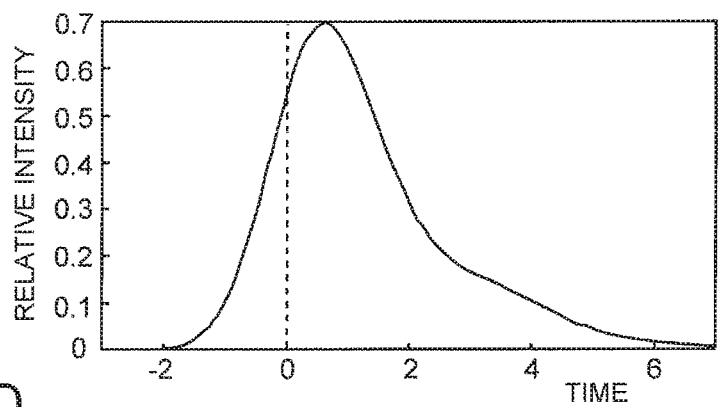
Figure 14D:
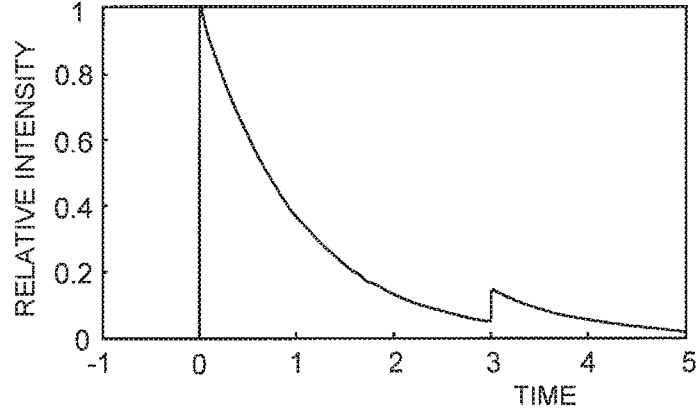

Subsequently, EM step processing in the PCA dimension is executed (step S24). That is, as illustrated in FIG. 11, in the E step, the signal division by the equal division and the signal division by the proportional division are selectively executed in accordance with the number of repetitions (steps S241 to S243), and in the M step, the process of the m-Gaussian distribution M step is executed (step S244). Then, a determination is made as to whether an estimated spectrum has converged (step S245), and when the estimated spectrum is determined to converge, a determination is made as to whether an excessive division occurs by, for example, determining whether there is a significantly unstable solution, and it correlates the spectrum to a certain degree or more, as described above (step S246). When an excessive division is determined to occur, the integrating process for integrating a plurality of peak models is performed to reduce the number of peak models (step S247), and the processing returns to step S241. Meanwhile, when no excessive division is determined to occur in step S246, the processing is finished since the model integration is not needed.

When a solution is obtained in the PCA dimension in such a manner, the dimensional compression of the PCA is cancelled, so that the solution is expanded on a spectrum in a real dimension (step S25). Then, the peak separation is executed again by the EM step according to the flowchart illustrated in FIG. 12 in the real dimension, which is the same the flowchart illustrated in FIG. 11 (step S26). In the real dimension, the addition of a peak model is not executed, only a simple repetition of the EM step and the integration of peak models are executed. For this reason, it is possible to improve the accuracy of the peak separation without taking a long time to execute the EM step in the real dimension.

Of course, rather than executing the process in the PCA dimension and the process in the real dimension in combination as in the embodiment described above, the peak separation may be performed by only the process in PCA dimension, or conversely, the peak separation may be performed only the process in the real dimension. The former is effective in shortening a processing time, and the latter has an advantage in the simplicity of implementation by not executing the PCA dimensional compression and its cancellation and in the accuracy of the peak separation.

Figure 1:
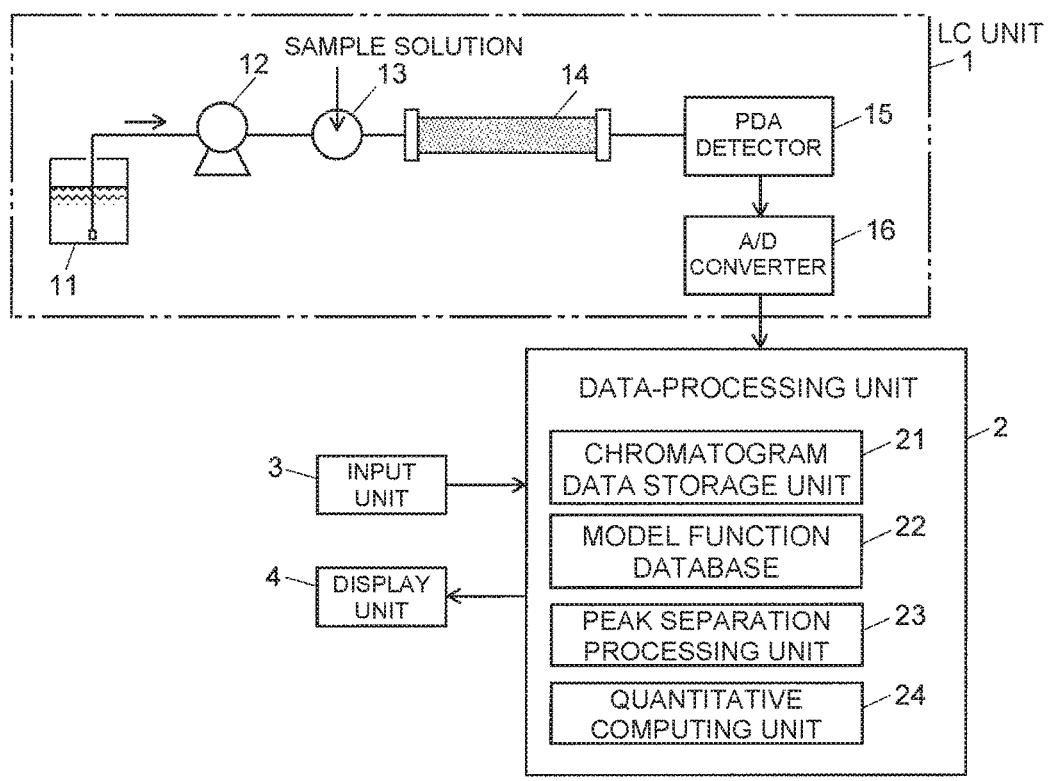
FIG. 1 is a schematic configuration diagram illustrating an example of a liquid chromatograph system including a chromatogram data processing apparatus for performing a chromatogram data processing method according to the present invention.

Subsequently, description will be made about an example of an LC analyzer that includes a chromatogram data processing apparatus for executing the chromatogram data processing method described with reference to FIG. 2. FIG. 1 is a schematic configuration diagram of this LC analyzer. The configuration and an abbreviated operation of this LC analyzer will be described.

This LC analyzer includes an LC unit 1 and a data-processing unit 2. In the LC unit 1, a solvent delivery pump 12 sucks a mobile phase from a mobile phase container 11 and supplies it to an injector 13 at a certain flow rate. The injector 13 injects a sample solution into the mobile phase with a predetermined timing. The injected sample solution is pushed by the mobile phase to be introduced in a column 14, and components in the sample solution are separated in a time direction while the sample solution passes through the column 14, and eluted from the outlet of the column 14. A PDA detector 15 disposed at the outlet of the column 14 repeatedly measures an absorbance distribution in a predetermined wavelength range for the eluate that is introduced one by one with time. A signal obtained by this measurement is converted into a digital signal by an analog/digital (A/D) converter 16, and input into the data-processing unit 2 in the form of three dimensional chromatogram data.

The data-processing unit 2 includes functional blocks such as a chromatogram data storage unit 21 for storing three dimensional chromatogram data, a model function database 22 in which various modified Gaussian distribution model waveforms and the like are stored, a peak separation processing unit 23 for executing the peak separation processing based on the EM algorithm for a GMM as described above on three dimensional chromatogram data, a quantitative computing unit 24 for performing quantitative calculation based on a chromatogram peak separated for each component. The data-processing unit 2 is connected to, for example, an input unit 3 for allowing an analyst to specify various parameters necessity for the data processing, and a display unit 4 for displaying peak separation results, quantitative computation results, and the like.

In the LC analyzer according to the present embodiment, when three dimensional chromatogram data collected by the LC unit 1 for one sample is once stored in the chromatogram data storage unit 21 as one data file, and an analyst issues instructions to start the execution of the peak separation processing or the like after specifying the data file to be processed on the input unit 3, the peak separation processing unit 23 executes the processing described above using the model function database 22, so as to estimate a chromatogram waveform and a spectrum waveform separated for each component. The quantitative computing unit 24 calculates the area of a peak on the estimated chromatogram waveform, and calculates a quantitative value based on the area value.

In the LC analyzer according to the present embodiment, even in the case where a target component and another component are not separated sufficiently from each other in the LC unit 1, the waveform of the chromatogram peak of the target component is determined in the data-processing unit 2 with high accuracy, and thus it is possible to calculate the concentration of the target component accurately.

It should be noted that the chromatogram data processing method and the LC analyzer in the embodiments described above is a mere example of the present invention, and any change, addition or modification appropriately made within the spirit of the present invention will evidently fall within the scope of claims of the present patent application.

For example, a detector of a chromatograph for acquiring three dimensional chromatogram data to be processed in the present invention does not have to be the multichannel detector such as the PDA detector described above, and may be an ultraviolet-visible spectrophotometer, an infrared spectrophotometer, a near-infrared spectrophotometer, and a fluorescence spectrophotometer capable of high-speed wavelength scanning. In addition, a liquid chromatograph mass spectrometer or a gas chromatograph mass spectrometer including a mass spectrograph as a detector may be employed.

In addition, data obtained by detecting a sample introduced by the flow injection analysis (FIA) method using a PDA detector or the like, rather than the analysis through a column, is three dimensional data having three dimensions: time, wavelength, and absorbance, and is substantially the same as three dimensional chromatogram data collected using a liquid chromatograph. Therefore, it is evident that the present invention is applicable to apparatuses for processing such data.

REFERENCE SIGNS LIST

1 . . . LC Unit
11 . . . Mobile Phase Container
12 . . . Solvent Delivery Pump
13 . . . Injector
14 . . . Column
15 . . . PDA Detector
16 . . . Analog/digital Converter
2 . . . Data-processing Unit
21 . . . Chromatogram Data Storage Unit
22 . . . Model Function Database
23 . . . Peak Separation Processing Unit
24 . . . Quantitative Computing Unit
3 . . . Input Unit
4 . . . Display Unit

The invention claimed is:

1. A chromatogram data processing method for processing three dimensional chromatogram data that is collected for a sample to be measured and has dimensions of time, signal intensity, and a third dimension, the chromatogram data processing method performing peak model function fitting in two steps so as to separate peaks originating from a plurality of components contained in the sample, the peaks overlapping one another on a chromatogram having axes representing time and signal intensity, respectively, the chromatogram data processing method comprising:

a) a data dividing step of dividing given three dimensional chromatogram data for one or more components and determining three dimensional chromatogram data for each component, based on a waveform profile model, the waveform profile model being for a chromatogram waveform profile of a chromatogram having axes representing time and signal intensity, respectively, and a spectrum waveform profile of a spectrum having axes representing third dimension and signal intensity, respectively;

b) a fitting step of, on a chromatogram and a spectrum determined from the three dimensional chromatogram data for each component obtained by the data dividing step, performing fitting of the chromatogram waveform profile and the spectrum waveform profile so as to correct parameters of a waveform profile model corresponding to each component, the fitting step alternatingly repeating a first step and a second step, the first step being a step of determining a spectrum waveform by a least squares method on assumption that the chromatogram waveform profile is correct, the second step being a step of determining a chromatogram waveform by least squares method on assumption that the spectrum waveform profile is correct, so as to increase a likelihood of the fitting; and c) a contained component determining step of repeatedly performing the data dividing step and the fitting step a specified number of times or until a solution converges, then filtering the given three dimensional chromatogram data so as to extract or enhance a spectrum component orthogonal to a spectrum corresponding to each component obtained at a time point, and determining whether still another component is contained in the sample based on a height of a peak-like waveform appearing in data after the filtering;

when the dividing step is performed a first time, the waveform profile model is an estimation result given in advance and when the dividing step is performed subsequently, the waveform profile model is an estimation result of the fitting step.

2. The chromatogram data processing method according to claim 1, wherein
when it is determined that another component is contained in the sample, the contained component determining step provides the peak-like waveform appearing in the data after the filtering for processing by the data dividing step, as an initial value of a chromatogram waveform profile of said another component to be added.

3. The chromatogram data processing method according to claim 1, wherein
the data dividing step switches between proportional division and equal division in accordance with a number of repetitions of a step for peak separation processing or how a solution converges, the proportional division dividing a residue signal in accordance with an intensity ratio of a theoretical value at each measurement point, the residue signal being determined by subtracting from the given three dimensional chromatogram data a theoretical value of a signal intensity calculated based on each chromatogram waveform and each spectrum waveform, the equal division dividing the residue signal equally for each component.

4. The chromatogram data processing method according to claim 1, wherein
the data dividing step divides a residue signal in accordance with least squares approximation using a linear sum of spectra for components, the residue signal being determined by subtracting from the given three dimensional chromatogram data a theoretical value of a signal intensity calculated based on each chromatogram waveform and each spectrum waveform.

5. The chromatogram data processing method according to claim 4, wherein
in executing the least squares approximation, a weight given to a spectrum of each component is limited using one or both of a size of the residue signal and a size of the theoretical value of the signal intensity of each component.

6. The chromatogram data processing method according to claim 1 further comprising:
   d) an estimating step of determining a chromatogram waveform by adding a chromatogram waveform of each component at an arbitrary ratio, and estimating a stability of a solution by an EM algorithm performed by the data dividing step and the fitting step based on a difference between an intensity on the chromatogram waveform and the theoretical value of the signal intensity.

7. The chromatogram data processing method according to claim 1, wherein
   the fitting step uses a database in which chromatogram waveforms each having a peak width and a peak height that are normalized are stored, and selects and uses an optimal chromatogram waveform from the database.

8. The chromatogram data processing method according to claim 1, wherein
   determination is made as to whether the peak-like waveform is attributable to linearity degradation of a detector based on a ratio of a size of each element in an eigenvalue obtained by performing principal component analysis on the data after the filtering in a form of a matrix, and it is concluded that there is no component to be added when the peak-like waveform is estimated to be attributable to the linearity degradation.

9. A chromatogram data processing apparatus for processing three dimensional chromatogram data that is collected for a sample to be measured and has dimensions of time, signal intensity, and a third dimension, the chromatogram data processing apparatus performing peak model function fitting in two steps so as to separate peaks originating from a plurality of components contained in the sample, the peaks overlapping one another on a chromatogram having axes representing time and signal intensity, respectively, the chromatogram data processing apparatus comprising:
   a) a data dividing unit for dividing given three dimensional chromatogram data for one or more components and determining three dimensional chromatogram data for each component, based on a waveform profile model, the waveform profile model being for a chromatogram waveform profile of a chromatogram having axes representing time and signal intensity, respectively, and a spectrum waveform profile of a spectrum having axes representing third dimension and signal intensity, respectively;
   b) a fitting unit for, on a chromatogram and a spectrum determined from the three dimensional chromatogram data for each component obtained by the data dividing step, performing fitting of the chromatogram waveform profile and the spectrum waveform profile so as to correct parameters of a waveform profile model corresponding to each component, the fitting unit alternatingly repeating a first step and a second step, the first step being a step of determining a spectrum waveform by a least squares method on assumption that the chromatogram waveform profile is correct, the second step being a step of determining a chromatogram waveform by least squares method on assumption that the spectrum waveform profile is correct, so as to increase a likelihood of the fitting; and
   c) a contained component determining unit for performing processing by the data dividing unit and processing by the fitting unit a specified number of times or until a solution converges, then filtering the given three dimensional chromatogram data so as to extract or enhance a spectrum component orthogonal to a spectrum corresponding to each component obtained at a time point, and determining whether still another component is contained in the sample based on a height of a peak-like waveform appearing in data after the filtering;
when the dividing step is performed a first time, the waveform profile model is an estimation result given in advance and when the dividing step is performed subsequently, the waveform profile model is an estimation result of the fitting step.

* * * * *